United States Patent [19]

Pontoglio et al.

[11] 4,012,441
[45] Mar. 15, 1977

[54] SULPHONIC DERIVATIVES HAVING THE STRUCTURE OF POLYOXAPOLYFLUOROALKANES

[75] Inventors: Enrico Pontoglio, Bollate (Milan); Ezio Strepparola, Treviglio (Bergamo); Giancarlo Bernardi, Canzo (Como), all of Italy

[73] Assignee: Montedison Fibre S.p.A., Milan, Italy

[22] Filed: May 22, 1975

[21] Appl. No.: 579,943

[30] Foreign Application Priority Data

May 30, 1974 Italy .................... 23340/74

[52] U.S. Cl. .................... 260/513 R; 260/503; 260/512 R; 260/512 C; 252/89 R; 252/552; 252/351
[51] Int. Cl.² .................... C07C 143/08
[58] Field of Search .................... 260/513 F, 535 H

[56] References Cited

UNITED STATES PATENTS

| | | | |
|---|---|---|---|
| 3,301,893 | 1/1967 | Putnam et al. | 260/513 F |
| 3,642,880 | 2/1972 | Sweeney et al. | 260/513 F |
| 3,715,378 | 2/1973 | Sianesi et al. | 260/535 H |
| 3,821,290 | 6/1974 | Anello et al. | 260/513 F |
| 3,847,978 | 11/1974 | Sianesi et al. | 260/535 H |

OTHER PUBLICATIONS

Guenthner et al., Ind. Eng. Chem., Prod. Research and Develop., 1, 165 (1962).

*Primary Examiner*—Bernard Helfin
*Assistant Examiner*—Nicky Chan
*Attorney, Agent, or Firm*—Hubbell, Cohen, Stiefel & Gross

[57] ABSTRACT

Disclosed are alkali and ammonium polyoxapolyfluoroalkanesulphonates having the formula:

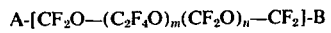

A-[CF$_2$O—(C$_2$F$_4$O)$_m$(CF$_2$O)$_n$—CF$_2$]-B and the free acids thereof, in which the oxyperfluoroalkylene units —C$_2$F$_4$O— and —CF$_2$O— are randomly distributed along the chain; $m$ and $n$ are integers the sum of which is a number from 2 to 50, and preferably from 4 to 20; the $m/n$ ratio is between 0.2 and 1.5; A is a monovalent radical —CH$_2$O—R—SO$_3$M, wherein R is a divalent radical in alpha-gamma or alpha-delta position and is selected from the group consisting of alkylene, cycloalkylene, arylene and benzylene radicals, optionally containing, as substituents, chlorine atoms or alkylene or alkoxy groups; and M is an alkali metal, hydrogen or an ammonium group; and B is the same as A or is the radical —CH$_2$OH. These products are prepared by reacting α,ω-bis(hydroxymethyl)polyoxaperfluoroalkanes having the formula

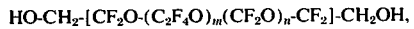

HO-CH$_2$-[CF$_2$O-(C$_2$F$_4$O)$_m$(CF$_2$O)$_n$-CF$_2$]-CH$_2$OH, or the alkali or ammonium dialcoholates thereof, with a sultone of the formula

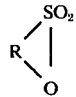

wherein R is a divalent radical in alpha-gamma or alpha-delta position and is selected from the group consisting of alkylene, cycloalkylene, arylene and benzylene radicals.

3 Claims, No Drawings

SULPHONIC DERIVATIVES HAVING THE STRUCTURE OF POLYOXAPOLYFLUOROALKANES

This invention relates to a new class of surfactants characterized by high thermal and chemical stability and having the structure of polyoxapolyfluoroalkanes with sulphonic end groups, and to the processes for the preparation thereof.

Surface-active compounds whose structure consists of a fluorocarbon chain of hydrophobic nature having at one end a polar group of hydrophilic nature such as, for example, a carboxylic function (optionally in the form of a salt), a sulphonic function, an ammonium group of cationic nature, are already known in the art.

Compounds of this type are described, for example, by J. N. Simons, "Fluorine Chemistry", Academic Press., New York, 1964, Vol. V Page 370, and by N. L. Jarvis & W. A. Zisman in "Surface Chemistry of Fluoro Chemicals" in Kirk-Othmer, Encyclopedia of Chemical Technology, 2nd Edition, Interscience Publishers, New York, 1966, Vol. 9, page 707. Such classes of surfactants are characterized a hydrophobic end group such as e.g. the groups $-CF_3$, $-CF_2H$, $-CF_2Cl$.

It has recently been disclosed that it is possible to use, as surfactants, compounds having the structure of polyoxaperfluoroalkanes, with hydrophilic terminal groups at both ends of the molecule. As described in U.S. Pat. No. 3,847,978 and in U.S. patent application Ser. No. 536,951 filed on Dec. 23, 1974, the surfactants of this type have the formula

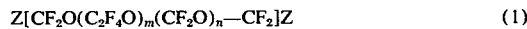  (1)

$$Z[CF_2O(C_2F_4O)_m(CF_2O)_n-CF_2]Z$$

wherein the oxyperfluoroalkylene units $-C_2F_4O-$ and $-CF_2O$ are randomly distributed along the chain; $m$ and $n$ are integers the sum of which is a number from 2 to 50 and wherein the $m/n$ ratio is between 0.2 and 1.5; and Z is a carboxylic group $-COOH$ (optionally in the form of a salt) or one of the groups

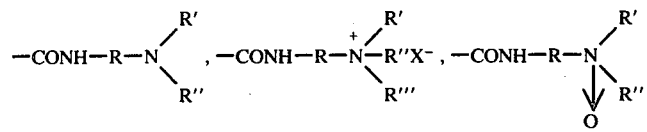

wherein R', R'', R''' are alkyl radicals, R is a divalent radical having the structure $-(CH_2)_p-$, wherein $p$ is an integer from 1 to 20, and $X^-$ is an anion.

It has now been discovered, in accordance with the present invention, that there is a new class of compounds having the characteristics of surfactants which — in spite of their substantially polyoxapolyfluoroalkane structure — exhibit, in comparison with the compounds described in the above-cited U.S. patent and U.S. patent application, a higher thermal and chemical stability as well as a higher solubility in water and in polar solvents, and which furthermore, retain a high surface-active power even in a strongly acid medium and/or in the presence of metal cations, especially in the presence of $Ca^{++}$ ions.

These new compounds have the formula:

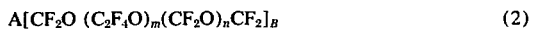  (2)

$$A[CF_2O\ (C_2F_4O)_m(CF_2O)_nCF_2]_B$$

wherein A is a monovalent radical $-CH_2O-R-SO_3M$, in which R is a divalent radical in alpha-gamma or alpha-delta position and is selected from the group consisting of alkylene, cycloalkylene, arlyene and benzylene radicals; M is an alkali metal or a hydrogen atom or an ammonium group; B is the same as A, or is the radical $-CH_2OH$; the oxyperfluoroalkylene units $-C_2F_4O-$ and $-CF_2O-$ are randomly distributed along the chain; $m$ and $n$ are integers the sum of which is a number from 2 to 50; and the $m/n$ ratio is between 0.2 and 1.5. The radicals R may contain substituents such as halogen atoms or alkoxy radicals.

According to a further feature of the present invention, the aforesaid compounds are obtained by reacting α,ω-bis-(hydroxymethyl)polyoxaperfluoroalkanes having the formula

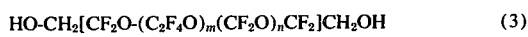  (3)

$$HO-CH_2[CF_2O-(C_2F_4O)_m(CF_2O)_nCF_2]CH_2OH$$

with a sultone of the formula

in which R is as defined above for the compounds of formula (2).

The diols of formula (3) can be readily obtained from the corresponding dicarboxylic acids or from derivatives thereof, such as methyl esters or acyl halides, according to conventional methods; for instance by reduction with simple or complex hydrides, such as e.g. $LiAlH_4$, in the presence of a dissolving or dispersing agent, or by catalytic reduction with hydrogen. The corresponding polyoxapolyfluoroalkane dicarboxylic acids can be obtained, according to U.S. Pat. No. 3,847,978, by reductive cleavage of the polyperoxidic-perfluoropolyethers derived from the photo-oxidation of tetrafluoroethylene, according to U.S. Pat. No. 3,715,378.

The above sultones, i.e., intermolecular esters of hydroxysulphonic acids corresponding to the following formula.

wherein R is as defined above, represent a known class of compounds, available commercially and easily obtainable by synthesis according to known methods. Some representative examples of the hydroxysulphonic acids are:

3-hydroxy-1-propanesulphonic acid, 4-hydroxy-1-butanesulphonic acid, 3-hydroxy-1-octanesulfonic acid, 3-hydroxy-1-cyclopropanesulphonic acid, 1,2-dimethyl-3-hydroxy-1-butanesulphonic acid, 1,1,2,2-tetrachloro-3-hydroxy-1-propanesulfonic acid, 2- hydroxy-alphatoluenesulphonic acid, alpha-hydroxy-2-toluenesulphonic acid, 8-hydroxy-1-naphthalenesulphonic acid, etc.

The $\alpha,\omega$-bis(hydroxymethyl)polyoxaperfluoroalkanes, corresponding to formula (3), can be employed in the reaction in pure chemical form, or in admixture with products different from one another as regards the values of the indices $m$ and $n$, within the limits specified above.

The reaction between the $\alpha,\omega$-bis(hydroxymethyl)-polyoxaperfluoroalkanes and the sultones can be conducted with the aforementioned diols in the free state. However, it is preferable to employ them in the form of their alkali alcoholates.

The reaction employing the aforesaid diols in the free state is generally conducted in the presence of basic compounds such as, for example, anhydrous sodium carbonate; it may be conducted in the absence of solvents, or in solvents of the ether type, such as ethyl ether, dioxane, tetrahydrofuran, or in aromatic solvents such as benzene or toluene.

A preferred embodiment of the present invention consists in reacting with a sultone the $\alpha,\omega$-bis(hydroxymethyl)polyoxaperfluoroalkanes in the form of their alkali alcoholates. In such case, an excess of the sultone itself can be used as a dispersant, or a primary, secondary or, preferably, a tertiary alcohol as a solvent; the sulphonic reaction product, corresponding to formula (2), is obtained in the form of e.g. the sodium salt.

The molar ratios between the sultone and the $\alpha,\omega$-bis(hydroxymethyl)polyoxaperfluoroalkane may range from 0.5 to 20. Depending on such ratio and on the reaction conditions, it is possible to obtain compounds of formula (2) in which B is the same as A, or in which B is the —$CH_2OH$ group as shown above.

The reaction temperature may range from 0° to 150° C, also depending on the solvent employed, the preferred temperature being between 30° and 70° C.

The polyoxapolyfluoroalkanesulphonic acid and the alkali salts thereof exhibit interesting properties as surfactants, soluble in water, alcohols and solutions of neutral or acidic concentrated electrolytes, such as sodium chloride, sulphuric acid and hydrochloric acid; furthermore they are soluble in aqueous alkali solutions. These characteristics render them highly suitable as surface-active, wetting, flotation, emulsifying and dispersing agents, in particular in the polymerization of aqueous emulsions of olefins and fluoroolefins, for instance ethylene and tetrafluoroethylene, as well as levelling agents, detergents and corrosion inhibitors.

The following examples are merely illustrative and are not to be regarded as limiting the scope of this invention.

EXAMPLE 1

4.74 g. of a mixture of diols having formula (3), i.e.
HO—$CH_2[CF_2O—(C_2F_4O)_m(CF_2O)_nCF_2]CH_2OH$,
wherein the $m/n$ ratio was 0.9 and the average molecular weight 474, determined according to the method described by J. Dandoy, A. Alloing-Bernard & C. Renson-Deneubourg in Ind. Chim. Belg. 36, 689–693 (1971), were introduced, in a dry nitrogen atmosphere, into a pyrex glass three-neck reactor having a 250 ml capacity, equipped with magnetic stirrer and reflux condenser.

1.95 g of sodium t-butylate dissolved in 50 ml of anhydrous t-butyl alcohol were added thereto.

The reaction was conducted for 2 hours at 30° C, whereupon 2.47 g of 1,3-propanesultone were admixed therewith and the whole reacted for a further 8 hours at 50° C.

The appearance of a white precipitate was observed in the course of the reaction.

At the end of the reaction and after removal of the t-butyl alcohol by distillation under a reduced pressure of 15 torr, the residue was washed with benzene and ethyl ether.

After drying by means of a mechanical pump (0.1 torr) at 50° C, 5.1 g of a white crystalline solid were obtained. This solid was completely soluble in water, showing a neutral reaction upon testing with litmus paper, and also soluble in aqueous solutions of acids and bases, as well as in alcohols.

Nuclear magnetic resonance and infrared spectroscopic analyses revealed the following structure of the product: $NaO_3S(CH_2)_3OCH_2—[CF_2O—(C_2F_4O)_m(CF_2O)_nCF_2]CH_2O(CH_2)_3SO_3Na$, in which $m/n = 0.9$.

The product proved to highly surface-active, as shown by the data reported below, which relate to the surface tension of aqueous solutions thereof at different concentrations:

| Concentration (% by weight) | Surface tension at 20° C (dynes/cm) |
| --- | --- |
| 0.001 | 55 |
| 0.01 | 38 |
| 0.1 | 25 |

The product, when dissolved in $H_2SO_4$ at 50% by weight, proved to be capable of lowering the surface tension of the solution to 25 dynes/cm at 20° C, even at concentrations as low as 0.01% by weight. The original aqueous solution at 50% by weight of $H_2SO_4$ exhibited a surface tension of 79.2 dynes/cm.

EXAMPLE 2

Following the same procedures as in Example 1, 10.6 g of a mixture of diols corresponding to formula (3), having an $m/n$ ratio = 1.2 and an average molecular weight of 1060, were reacted with 1.97 g of sodium t-butylate dissolved in 100 ml of t-butyl alcohol and then with 2.47 g of 1,3-propanesultone. 10.2 g of a white powder were obtained. This was soluble in water with a neutral reaction to litmus paper, and soluble in aqueous solutions of alkalis and acids as well as in alcohols.

The compound had the structure shown in formula (2), wherein A = B = —$CH_2O(CH_2)_3SO_3Na$ and $m/n$ = 1.2.

A 2% solution by weight of the product exhibited a surface tension of 28 dynes/cm at 20° C.

The compound, when dissolved in a 0.5% by weight solution of $H_2SO_4$ at 10%, lowered the solution surface tension to 25 dynes/cm at 20° C. The original aqueous solution of $H_2SO_4$ at 10% by weight had a surface tension of 73 dynes/cm.

A calorimetric analysis of a sample of the salt, carried out by means of thermal analyzer Du Pont 900 (DSC modulus — heating rate = 10° C/min) revealed that decomposition started around 340° C, while a sample of sodium salt consisting of the mixture of polyoxaperfluoroalkandioic acids having the same average molecular weight began to decompose at about 200° C.

EXAMPLE 3

By operating as in Example 1, 15.9 g of a mixture of diols corresponding to formula (3) with an $m/n$ ratio = 1, and having an average molecular weight of 2250, salified with an equivalent amount of sodium t-butylate, were reacted with 1.72 g of 1,3-propanesultone dissolved in 100 ml of t-butyl alcohol for 2 days at 50° C. 12.2 g of a white product in powder form were thus obtained.

This product was slightly soluble in water and alcohol. Elemental analysis showed a content of C, F and S of 20.95%, 53.9% and 2.45%, respectively (theoretical values: for C: 20.85%, for F: 54.2%, for S: 2.52%), these values being in accordance with the structure corresponding to the average formula:

$$NaO_3(CH_2)_3OCH_2CF_2O[C_2F_4O]_{11.4}(CF_2O)_{11.4}]CF_2CH_2O(CH_2)_3SO_3Na$$

An aqueous solution at 0.1% by weight of the product exhibited a surface tension of 45 dynes/cm at 20° C.

A calorimetric analysis, carried out as described in Example 2, revealed that decomposition began at about 340° C.

EXAMPLE 4

The purpose of this example is to show the use of primary alcohol solvents in the reaction between the salified diol and the 1,3-propanesultone.

In a 250 ml glass reactor equipped with magnetic stirrer, reflux condensor and thermometer, 7.17 g of the same diol as in Example 2, and having an average molecular weight of 1060, were salified — operating with a dry nitrogen flow — by reaction with 0.703 g of sodium methylate dissolved in 70 ml of $CH_3OH$. 1.65 g of 1,3-propanesultone were subsequently admixed therewith and the whole mass was reacted at 30°–40° C for 8 hours, always in a dry nitrogen atmosphere. During this time period a white solid precipitated.

Precipitation was then completed by the addition of 100 ml of benzene. The precipitate was filtered, repeatedly washed with benzene and ethyl ether, and dried by means of a mechanical pump. The product so obtained weighed 5.1 g.

The nuclear magnetic resonance and infrared spectra revealed, on analysis, that the product corresponded to formula (2), the terminal group B being the same as A to the extent of 90%, the remaining 10% being —CH$_2$OH.

The product contained some impurities consisting of sodium methoxypropanesulphonate, while the product of Example 2 did not contain the corresponding sodium t-butoxypropanesulphonate.

EXAMPLE 5

5.25 g of sodium dialcoholate of a diol mixture the same as that employed in Example 2, and havng an average molecular weight of 1060 and an $m/n$ ratio of 1.2, were introduced into a 50 ml flask equipped with mechanical stirrer and thermometer.

11 g of 1,3-propanesultone were added thereto, whereupon the reaction was conducted for 16 hours at 50° C; during which time a white solid precipitated. At the end of the reaction the product was filtered, then purified with benzene in a continuous extractor in order to remove the impurities soluble in benzene.

There were thus obtained 4.6 g of a white powder having a structure corresponding to formula (2), wherein $A = B = CH_2O(CH_2)_3$—$SO_3Na$ and $m/n = 1.2$.

An aqueous solution at 2% by weight of this product exhibited a surface tension of 32 dynes/cm at 20° C.

EXAMPLE 6

This example was conducted in a 4000 ml stainless steel autoclave equipped with anchor stirrer, heating jacket and valves for the feeding of liquids and gas, and connected with pressure gauges and thermometers.

For the closed autoclave all traces of oxygen were removed by carrying out a series of nitrogen-vacuum operations. Subsequently, 1.1 g of the sodium polyoxapolyfluoroalkanesulphonate obtained in Example 1 and 0.055 g of ammonium persulphate dissolved in 2050 ml of distilled and previously deaerated water were introduced into the autoclave by means of liquid pumps.

Tetrafluoroethylene was introduced into the autoclave until a pressure of 20 atmospheres was reached. Then, having brought the internal liquid phase to a temperature of 30° C by means of external circulation of a thermoregulating liquid, 0.064 g of $(NH_4)_2SO_4$·$FeSO_4$·$6H_2O$ (Mohr salt) dissolved in 150 ml of water was introduced into the autoclave by means of a feed pump.

Polymerization was conducted for 40 minutes whereupon, after having removed the residual monomer, a stable colloidal aqueous dispersion of polytetrafluoroethylene was discharged from the autoclave.

EXAMPLE 7

Upon operating according to the same procedure as in Example 1, 4.6 g of a mixture of diols corresponding to formula (3), having an $m/n$ ratio of 0.9 and an average molecular weight of 474, in the form of sodium dialcoholates, were reacted with 3.01 g of tolysultone (intermolecular ester of alpha-hydroxy-2-toluenesulphonic acid) in 60 ml of t-butyl alcohol for 10 hours at 50° C.

After purification, 5.3 g of a white product in powder form were obtained. This was soluble in water and in methyl alcohol.

On the basis of infrared and nuclear magnetic resonance spectroscopic analyses, the formula $$NaO_3SC_6H_4CH_2OCH_2[CF_2O(C_2F_4O)_m(CF_2O)_nCF_2]CH_2O\ CH_2C_6H_4SO_3Na,$$

wherein the $m/n$ ratio is 0.9 and the average molecular weight is 858, was assigned to this product.

What is claimed is:

1. An alkali polyoxapolyfluoroalkanesulphonate having the formula:

$$A—[CF_2O—(C_2F_4O)_m(CF_2O)_n—CF_2]—B$$

or a free acid thereof, in which the oxyperfluoroalkylene units —$C_2F_4O$— and —$CF_2O$— are randomly distributed along the chain; $m$ and $n$ are integers whose sum is a number from 2 to 50; and the $m/n$ ratio is between 0.2 and 1.5; A is a monovalent radical —$CH_2O$—R—$SO_3M$, wherein R is propylene or butylene, M is an alkali metal or hydrogen; and B is the same as A or —$CH_2OH$.

2. A compound as defined in claim 1, wherein the sum of $m$ and $n$ is a number of 4 to 20.

3. A compound as defined in claim 1, wherein A and B are both $NaO_3S(CH_2)_3OCH_2$— and the $m/n$ ratio is 0.9.

* * * * *

UNITED STATES PATENT OFFICE
CERTIFICATE OF CORRECTION

Patent No. 4,012,441    Dated March 15, 1977

Inventor(s) Enrico Pontoglio et al.

It is certified that error appears in the above-identified patent and that said Letters Patent are hereby corrected as shown below:

Column 1, line 24: "a hydrophobic" should read -- by a hydrophobic; line 32: "this type" should read -- this new type --; line 62: "acid" should read -- acidic --.

Column 2, line 12: "atoms or alkoxy radicals." should read -- atoms or alkyl or alkoxy radicals. --.

Column 4, line 21: "proved to highly" should read -- proved to be highly --; line 55: "A 2% solution" should read -- A 2% aqueous solution --.

Column 6, line 12: "For" should read -- From --; line 37: "tolysultone" should read -- tolylsultone --.

Signed and Sealed this

Seventh Day of June 1977

[SEAL]

Attest:

RUTH C. MASON
*Attesting Officer*

C. MARSHALL DANN
*Commissioner of Patents and Trademarks*